(12) United States Patent
Malefyt et al.

(10) Patent No.: US 10,555,522 B2
(45) Date of Patent: Feb. 11, 2020

(54) LONG TERM METHODS OF IMPROVING DISEASE TOLERANCE IN PLANTS

(71) Applicant: AgroFresh Inc., Collegeville, PA (US)

(72) Inventors: Timothy Malefyt, Stroudsburg, PA (US); Alan Green, Des Moines, IA (US)

(73) Assignee: AgroFresh Inc., Collegeville, PA (US)

( * ) Notice: Subject to any disclaimer, the term of this patent is extended or adjusted under 35 U.S.C. 154(b) by 0 days.

(21) Appl. No.: 15/460,957

(22) Filed: Mar. 16, 2017

(65) Prior Publication Data

US 2017/0265462 A1 Sep. 21, 2017

Related U.S. Application Data

(60) Provisional application No. 62/310,031, filed on Mar. 18, 2016.

(51) Int. Cl.
*A01N 27/00* (2006.01)

(52) U.S. Cl.
CPC .................... *A01N 27/00* (2013.01)

(58) Field of Classification Search
None
See application file for complete search history.

(56) References Cited

U.S. PATENT DOCUMENTS

| | | | |
|---|---|---|---|
| 5,518,988 A | 5/1996 | Sisler et al. | |
| 6,017,849 A | 1/2000 | Daly et al. | |
| 8,377,489 B2* | 2/2013 | Edgington | A01N 3/00 426/271 |
| 9,055,741 B2* | 6/2015 | Bardella | A01N 27/00 |
| 2007/0265166 A1 | 11/2007 | Bardella et al. | |
| 2012/0009238 A1 | 1/2012 | Brahm et al. | |
| 2013/0298290 A1* | 11/2013 | Haas | A01N 25/02 800/298 |
| 2015/0272115 A1 | 10/2015 | Green | |
| 2015/0282479 A1 | 10/2015 | Basel et al. | |

FOREIGN PATENT DOCUMENTS

| | | | |
|---|---|---|---|
| CN | 102715160 | * | 10/2012 |
| EP | 2392210 | * | 6/2010 |
| IN | 2007DE01009 | * | 8/2007 |
| WO | WO 02068609 | * | 9/2002 |
| WO | WO 2009002407 | * | 12/2008 |

OTHER PUBLICATIONS

Veselova et al.( Roles of ethylene and cytokinins in development of defense responses in Triticum aestivum plants infected with Septoria nodorum, Russian Journal of Plant Physiology (2016), 63(5), 609-619 ).*
Veselova et al. ( The effect of 1-methylcyclopropene on the components of pro- and antioxidant systems of wheat and the development of defense reactions in fungal pathogenesis, Applied biochemistry and microbiology (2014), vol. 50, No. 5, pp. 516-523).*
Sosnoskie, Breaking Bindweed: Deciphering the complex interactions among weed water, herbicide, and crop to improve Convolvulous arvensis control in processing tomato, Sosnoskie et al., California Tomato Research Institute, 2015 (Year: 2015).*
International Search Report and Written Opinion, International Application No. PCT/US2017/021527, search completed Apr. 25, 2017, 10 pages.
Su et al., "Effect of 1-methylcyclopropene (1-MCP) on reducing postharvest decay in tomatoes (*Solanum lycopersicum* L. )", Postharvest Biology and Technology, 2011, vol. 64, Issue 1, pp. 133-137.

* cited by examiner

*Primary Examiner* — Alton N Pryor
(74) *Attorney, Agent, or Firm* — Barnes & Thornburg LLP

(57) ABSTRACT

The present disclosure provides methods of improving disease tolerance of a crop plant by improving and/or inducing long-term disease tolerance of the crop plants against one or more of fungal, bacterial, and viral diseases. The methods provided in the present disclosure have desirable properties and related advantages compared to other methods known in the art.

20 Claims, 1 Drawing Sheet

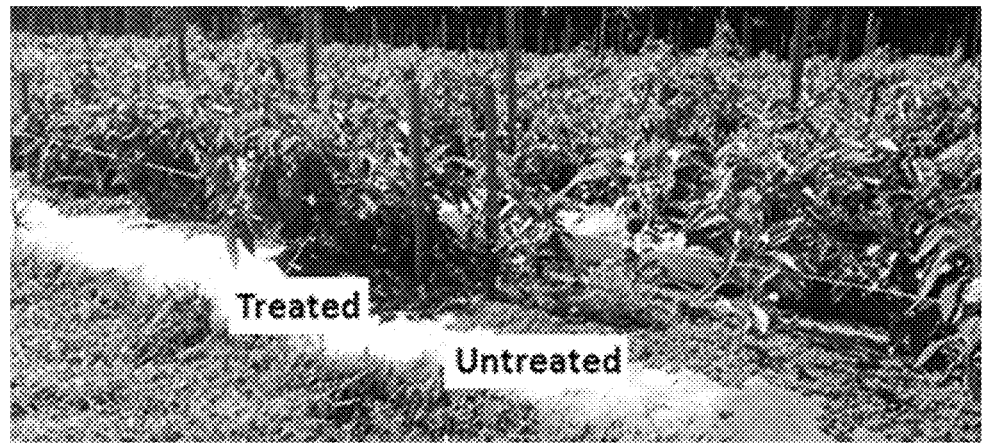

LONG TERM METHODS OF IMPROVING DISEASE TOLERANCE IN PLANTS

CROSS-REFERENCE TO RELATED APPLICATION

This application claims the benefit under 35 U.S.C. § 119(e) of U.S. Provisional Patent Application Ser. No. 62/310,031, filed on Mar. 18, 2016, the entire disclosure of which is incorporated herein by reference.

BACKGROUND OF THE INVENTION

In spite of strong plant breeding efforts against plant pathogens, plants continue to be susceptible to pathogenic diseases, including viral, bacterial and fungal organisms. Historically these plant pathogens have had devastating impact on entire nations, with the most extreme example being the Irish potato famine. Even today, many vegetable crops have been subjected to disastrous diseases, such as the recent tomato mosaic virus outbreak that destroyed plants in entire tomato greenhouses. As a result of these diseases, yields of vegetable crops are reduced and consumer prices increase dramatically.

To combat these problems, plants may be treated with chemical compositions in an attempt to provide protection from pests and diseases to promote improvements in yield, growth, and/or productivity. However, there is a continual need to develop new methods to improve the protection of plants from distinct types of pathogens such as fungal, bacterial, and viral diseases.

As evidenced by the $10 billion market for agricultural fungicides, nearly all plants are treated in an effort to control fungal infections. However, bacterial infections and viral infections in plants are much more difficult to contain. Although plant genetics, antibiotics, and insecticides can be tried in this regard, these methods only offer partial solutions to the problem. Therefore, it is highly desirable to provide compositions that offer disease tolerance for plants against one or more of fungal, bacterial, and viral diseases.

Furthermore, providing long-term improvement in plant disease tolerance is also extremely desirable. Methods that reduce the incidence and severity of diseases in plants in a convenient and lasting manner would be extremely advantageous. For instance, treatment of plants prior to shipment and transplantation of the plants to the field would provide a tremendous benefit to the industry.

Accordingly, the present disclosure provides methods of improving disease tolerance of a crop plant by improving and/or inducing long-term disease tolerance of the crop plants against one or more of fungal, bacterial, and viral diseases. The methods provided in the present disclosure have desirable properties and related advantages compared to other methods known in the art. First, the methods of the present disclosure are unexpectedly effective against multiple disease-causing agents such as fungi, bacteria, and viruses. Second, the methods of the present disclosure offer long-term protection against disease-causing agents, so that plants may be treated early in development and have observable disease resistance several weeks after application. Finally, the improvement in plant disease resistance may provide for higher yields of crops and require less pesticide use for growing plants. These combined benefits provide marked improvements over comparable methods known in the art.

SUMMARY OF THE INVENTION

Various embodiments of the invention are described herein as follows. In one aspect, a method of improving disease tolerance of a crop plant is provided. The method comprises the step of contacting the crop plant with a composition comprising at least one cyclopropene, wherein contacting the crop plant with the composition results in an improvement of long-term disease tolerance of the crop plant.

In another aspect, method of inducing disease tolerance of a crop plant is provided. The method comprises the step of contacting the crop plant with a composition comprising at least one cyclopropene, wherein contacting the crop plant with the composition results in an induction of long-term disease tolerance of the crop plant.

BRIEF DESCRIPTION OF THE DRAWING

FIG. 1 shows the differences in symptoms of fungal infection with Root Rot (*Pythium* sp.) on peppers approximately 60 days after transplantation. Differences may be observed between i) "Treated" plants (i.e., pepper plants sprayed with 1-MCP (1-10 g ai/ha prior to transplantation)) or ii) "Untreated" plants (i.e., pepper plants left untreated). Pepper plants were either sprayed with 1-MCP or left untreated as seedlings prior to transplantation.

DETAILED DESCRIPTION

The following numbered embodiments are contemplated and are non-limiting:

1. The method of clause 1, wherein the crop is a monocot crop.
2. The method of clause 1, wherein the crop is a dicot crop.
3. The method of clause 1, wherein the crop is corn.
4. The method of clause 1, wherein the crop is soybean.
5. The method of clause 1, wherein the crop is a vegetable.
6. The method of clause 1, wherein the crop is a solanaceous crop.
7. The method of clause 7, wherein the solanaceous crop is selected from the group consisting of tomato, pepper, eggplant, white potato, red potato, and tomatillo.
8. The method of clause 7, wherein the solanaceous crop is tomato.
9. The method of clause 7, wherein the solanaceous crop is pepper.
10. The method of clause 7, wherein the solanaceous crop is eggplant.
11. The method of clause 7, wherein the solanaceous crop is white potato.
12. The method of clause 7, wherein the solanaceous crop is red potato.
13. The method of clause 7, wherein the solanaceous crop is tomatillo.
14. The method of clause 1, wherein the crop is a member of the Cucurbitacea family.
15. The method of clause 15, wherein the member of the Cucurbitacea family is cucumber.
16. The method of clause 15, wherein the member of the Cucurbitacea family is melon.
17. The method of clause 15, wherein the member of the Cucurbitacea family is watermelon.
18. The method of clause 1, wherein the crop is a cruciferae crop.
19. The method of clause 19, wherein the cruciferae crop is cabbage.
20. The method of clause 19, wherein the cruciferae crop is broccoli.

21. The method of clause 19, wherein the cruciferae crop is cauliflower.

22. The method of any one of clauses 1 to 22, wherein the plant is a seedling.

23. The method of any one of clauses 1 to 23, wherein the plant is a pre-transplant plant.

24. The method of any one of clauses 1 to 24, wherein the cyclopropene is 1-methylcyclopropene (1-MCP).

25. The method of any one of clauses 1 to 25, wherein the composition is a liquid composition.

26. The method of clause 26, wherein the liquid composition further comprises a solvent.

27. The method of clause 27, wherein the solvent is water.

28. The method of any one of clauses 1 to 25, wherein the composition is a granular composition.

29. The method of clause 29, wherein the granular composition is a powder.

30. The method of any one of clauses 1 to 30, wherein the contacting is performed by a method selected from the group consisting of spraying, gassing, foaming, fogging, pouring, brushing, dipping, applying granules, similar methods, and combinations thereof.

31. The method of any one of clauses 1 to 30, wherein the contacting is performed via spraying.

32. The method of any one of clauses 1 to 30, wherein the contacting is performed via spreading.

33. The method of any one of clauses 1 to 30, wherein the contacting is performed via gassing.

34. The method of any one of clauses 1 to 30, wherein the contacting is performed via foaming.

35. The method of any one of clauses 1 to 30, wherein the contacting is performed via fogging.

36. The method of any one of clauses 1 to 30, wherein the contacting is performed via pouring.

37. The method of any one of clauses 1 to 30, wherein the contacting is performed via brushing.

38. The method of any one of clauses 1 to 30, wherein the contacting is performed via dipping.

39. The method of any one of clauses 1 to 30, wherein the contacting is performed via applying granules.

40. The method of any one of clauses 1 to 30, wherein the contacting is performed via a combination of one or more of spraying, gassing, foaming, fogging, pouring, brushing, dipping, applying granules.

41. The method of any one of clauses 1 to 41, wherein the long-term disease tolerance is a reduction in disease incidence of the crop plant.

42. The method of any one of clauses 1 to 42, wherein the long-term disease tolerance is a reduction in disease severity of the crop plant.

43. The method of any one of clauses 1 to 43, wherein the long-term disease tolerance is a fungal disease tolerance.

44. The method of clause 44, wherein the fungal disease is caused by a fungus selected from the group consisting of *Alternaria alternata* f. sp. *lycopersici, Colletotrichum coccodes, Colletotrichum dematium, Colletotrichum gloeosporioides, Glomerella cingulate, Alternaria alternate, Stemphylium botryosum, Pleospora tarda, Stemphylium herbarum, Pleospora herbarum, Pleospora lycopersici, Ulocladium consortiale, Stemphylium consortiale, Thielaviopsis basicola, Chalara elegans, Alternaria alternate, Phytophthora capsici, Phytophthora drechsleri, Phytophthora nicotianae* var. *parasitica, Phytophthora parasitica, Pseudocercospora fuligena, Cercospora fuligena, Macrophomina phaseolina, Pyrenochaeta lycopersici, Didymella lycopersici, Alternaria solani, Fusarium oxysporum* f. sp. *radicis-lycopersici, Fusarium oxysporum* f. sp. *lycopersici, Stemphylium botryosum* f. sp. *lycopersici, Stemphylium lycopersici, Stemphylium floridanum, Stemphylium solani, Botrytis cinerea, Botryotinia fuckeliana, Phytophthora infestans, Fulvia fulva, Cladosporium fulvum, Phoma destructiva, Oidiopsis sicula, Leveillula taurica, Pythium aphanidermatum, Pythium arrhenomanes, Pythium debaryanum, Pythium myriotylum, Pythium ultimum, Rhizoctonia solani, Thanatephorus cucumeris, Rhizopus stolonifer, Septoria lycopersici, Geotrichum candidum, Galactomyces geotrichum, Geotrichum klebahnii, Geotrichum penicillatum, Sclerotium rolfsii, Athelia rolfsii, Corynespora cassiicola, Verticillium albo-atrum, Verticillium dahliae, Sclerotinia sclerotiorum,* and *Sclerotinia minor.*

45. The method of clause 44, wherein the fungal disease is caused by a fungus selected from the group consisting of *Alternaria tomatophila, Pythium* sp., and *Pseudoperonospora cubensis.*

46. The method of any one of clauses 1 to 43, wherein the long-term disease tolerance is a bacterial disease tolerance.

47. The method of clause 47, wherein the bacterial disease is caused by a bacteria selected from the group consisting of *Clavibacter michiganensis* subsp. *michiganensis, Pseudomonas syringae* pv. *tomato, Xanthomonas campestris* pv. *vesicatoria, Erwinia carotovora* subsp. *carotovora, Ralstonia solanacearum, Pseudomonas corrugata,* and *Pseudomonas syringae* pv. *syringae.*

48. The method of clause 47, wherein the bacterial disease is caused by a bacteria selected from the group consisting of *Corynespora cassiicola, Xanthomonas euvesicatoria, Xanthomonas perforans,* [*Xanthomonas axonopodis* (syn. *campestris*) pv. *vesicatoria*], *Xanthomonas vesicatoria,* and *Xanthomonas gardneri.*

49. The method of any one of clauses 1 to 43, wherein the long-term disease tolerance is a viral disease tolerance.

50. The method of clause 50, wherein the viral disease is caused by a virus selected from the group consisting of tobacco mosaic virus (TMV), curly top virus, potato virus, pseudo curly top virus, tomato bushy stunt virus, tobacco etch virus, cucumber mosaic virus, tomato mosaic virus (ToMV), tomato mottle gemini virus, alfalfa mosaic virus, tomato spotted wilt virus, tomato yellow leaf curl virus, tomato yellow top virus.

51. The method of clause 50, wherein the viral disease is caused by a virus selected from the group consisting of Beet Curly Top Virus and Tomato Yellow Leaf Curl Virus.

52. The method of any one of clauses 1 to 49, wherein the long-term disease tolerance comprises a fungal disease tolerance and a bacterial disease tolerance.

53. The method of any one of clauses 1 to 46 or clauses 50 to 52, wherein the long-term disease tolerance comprises a fungal disease tolerance and a viral disease tolerance.

54. The method of clause any one of clauses 1 to 43 or clauses 47 to 54, wherein the long-term disease tolerance comprises a bacterial disease tolerance and a viral disease tolerance.

55. The method of any one of clauses 1 to 55, wherein the long-term disease tolerance comprises a fungal disease tolerance, a bacterial disease tolerance, and a viral disease tolerance.

56. The method of any one of clauses 1 to 56, wherein the long-term disease tolerance is conferred via contacting the crop plant with the composition prior to transplantation of the crop plant.

57. The method of any one of clauses 1 to 57, wherein the long-term disease tolerance is conferred via contacting the crop plant with the composition in a location selected from the group consisting of a greenhouse, a plant house, and an outdoor plant nursery.

58. The method of any one of clauses 1 to 57, wherein the long-term disease tolerance is conferred via contacting the crop plant with the composition in a greenhouse.

59. The method of any one of clauses 1 to 57, wherein the long-term disease tolerance is conferred via contacting the crop plant with the composition in a plant house.

60. The method of any one of clauses 1 to 57, wherein the long-term disease tolerance is conferred via contacting the crop plant with the composition in an outdoor plant nursery.

61. The method of any one of clauses 1 to 61, wherein the improvement of long-term disease tolerance improves crop plant yield.

62. The method of any one of clauses 1 to 62, wherein the improvement of long-term disease tolerance reduces pesticide use on the crop plant.

63. The method of any one of clauses 1 to 63, wherein the long-term disease tolerance is present between 6-12 weeks after contacting the crop plant with the composition.

64. The method of any one of clauses 1 to 64, wherein the long-term disease tolerance is present between 10-12 weeks after contacting the crop plant with the composition.

65. A method of inducing disease tolerance of a crop plant, said method comprising the step of: contacting the crop plant with a composition comprising at least one cyclopropene, wherein contacting the crop plant with the composition results in an induction of long-term disease tolerance of the crop plant.

66. The method of clause 66, wherein the crop is a monocot crop.

67. The method of clause 66, wherein the crop is a dicot crop.

68. The method of clause 66, wherein the crop is corn.

69. The method of clause 66, wherein the crop is soybean.

70. The method of clause 66, wherein the crop is a vegetable.

71. The method of clause 66, wherein the crop is a solanaceous crop.

72. The method of clause 72, wherein the solanaceous crop is selected from the group consisting of tomato, pepper, eggplant, white potato, red potato, and tomatillo.

73. The method of clause 72, wherein the solanaceous crop is tomato.

74. The method of clause 72, wherein the solanaceous crop is pepper.

75. The method of clause 72, wherein the solanaceous crop is eggplant.

76. The method of clause 72, wherein the solanaceous crop is white potato.

77. The method of clause 72, wherein the solanaceous crop is red potato.

78. The method of clause 72, wherein the solanaceous crop is tomatillo.

79. The method of clause 66, wherein the crop is a member of the Cucurbitacea family.

80. The method of clause 80, wherein the member of the Cucurbitacea family is cucumber.

81. The method of clause 80, wherein the member of the Cucurbitacea family is melon.

82. The method of clause 80, wherein the member of the Cucurbitacea family is watermelon.

83. The method of clause 66, wherein the crop is a cruciferae crop.

84. The method of clause 84, wherein the cruciferae crop is cabbage.

85. The method of clause 84, wherein the cruciferae crop is broccoli.

86. The method of clause 84, wherein the cruciferae crop is cauliflower.

87. The method of any one of clauses 66 to 87, wherein the plant is a seedling.

88. The method of any one of clauses 66 to 88, wherein the plant is a pre-transplant plant.

89. The method of any one of clauses 66 to 89, wherein the plant is a greenhouse plant.

90. The method of any one of clauses 66 to 90, wherein the cyclopropene is 1-methylcyclopropene (1-MCP).

91. The method of any one of clauses 66 to 91, wherein the composition is a liquid composition.

92. The method of clause 92, wherein the liquid composition further comprises a solvent.

93. The method of clause 93, wherein the solvent is water.

94. The method of any one of clauses 66 to 91, wherein the composition is a granular composition.

95. The method of clause 95, wherein the granular composition is a powder.

96. The method of any one of clauses 66 to 96, wherein the contacting is performed by a method selected from the group consisting of spraying, gassing, foaming, fogging, pouring, brushing, dipping, applying granules, similar methods, and combinations thereof.

97. The method of any one of clauses 66 to 96, wherein the contacting is performed via spraying.

98. The method of any one of clauses 66 to 96, wherein the contacting is performed via spreading.

99. The method of any one of clauses 66 to 96, wherein the contacting is performed via gassing.

100. The method of any one of clauses 66 to 96, wherein the contacting is performed via foaming.

101. The method of any one of clauses 66 to 96, wherein the contacting is performed via fogging.

102. The method of any one of clauses 66 to 96, wherein the contacting is performed via pouring.

103. The method of any one of clauses 66 to 96, wherein the contacting is performed via brushing.

104. The method of any one of clauses 66 to 96, wherein the contacting is performed via dipping.

105. The method of any one of clauses 66 to 96, wherein the contacting is performed via applying granules.

106. The method of any one of clauses 66 to 96, wherein the contacting is performed via a combination of one or more of spraying, gassing, foaming, fogging, pouring, brushing, dipping, applying granules.

107. The method of any one of clauses 66 to 107, wherein the long-term disease tolerance is a reduction in disease severity of the crop plant.

108. The method of any one of clauses 66 to 108, wherein the long-term disease tolerance is a fungal disease tolerance.

109. The method of clause 109, wherein the fungal disease is caused by a fungus selected from the group consisting of *Alternaria alternata* f. sp. *lycopersici, Colletotrichum coccodes, Colletotrichum dematium, Colletotrichum gloeosporioides, Glomerella cingulate, Alternaria alternate, Stemphylium botryosum, Pleospora tarda, Stemphylium herbarum, Pleospora* herbarum, *Pleospora lycopersici, Ulocladium consortiale, Stemphylium consortiale, Thielaviopsis basicola, Chalara elegans, Alternaria alternate, Phytophthora capsici, Phytophthora drechsleri, Phytophthora nicotianae* var. *parasitica, Phytophthora parasitica, Pseudocercospora fuligena, Cercospora fuligena,*

*Macrophomina phaseolina, Pyrenochaeta lycopersici, Didymella lycopersici, Alternaria solani, Fusarium oxysporum* f. sp. *radicis-lycopersici, Fusarium oxysporum* f. sp. *lycopersici, Stemphylium botryosum* f. sp. *lycopersici, Stemphylium lycopersici, Stemphylium floridanum, Stemphylium solani, Botrytis cinerea, Botryotinia fuckeliana, Phytophthora infestans, Fulvia fulva, Cladosporium fulvum, Phoma destructiva, Oidiopsis sicula, Leveillula taurica, Pythium aphanidermatum, Pythium arrhenomanes, Pythium debaryanum, Pythium myriotylum, Pythium ultimum, Rhizoctonia solani, Thanatephorus cucumeris, Rhizopus stolonifer, Septoria lycopersici, Geotrichum candidum, Galactomyces geotrichum, Geotrichum klebahnii, Geotrichum penicillatum, Sclerotium rolfsii, Athelia rolfsii, Corynespora cassiicola, Verticillium albo-atrum, Verticillium dahliae, Sclerotinia sclerotiorum*, and *Sclerotinia minor.*

110. The method of clause 109, wherein the fungal disease is caused by a fungus selected from the group consisting of *Alternaria tomatophila, Pythium* sp., and *Pseudoperonospora cubensis.*

111. The method of clause any one of clauses 66 to 108, wherein the long-term disease tolerance is a bacterial disease tolerance.

112. The method of clause 112, wherein the bacterial disease is caused by a bacteria selected from the group consisting of *Clavibacter michiganensis* subsp. *michiganensis, Pseudomonas syringae* pv. *tomato, Xanthomonas campestris* pv. *vesicatoria, Erwinia carotovora* subsp. *carotovora, Ralstonia solanacearum, Pseudomonas corrugata*, and *Pseudomonas syringae* pv. *syringae.*

113. The method of clause 112, wherein the bacterial disease is caused by a bacteria selected from the group consisting of *Corynespora cassiicola, Xanthomonas euvesicatoria, Xanthomonas perforans*, [*Xanthomonas axonopodis* (syn. *campestris*) pv. *vesicatoria*], *Xanthomonas vesicatoria*, and *Xanthomonas gardneri.*

114. The method of clause any one of clauses 66 to 108, wherein the long-term disease tolerance is a viral disease tolerance.

115. The method of clause 115, wherein the viral disease is caused by a virus selected from the group consisting of tobacco mosaic virus (TMV), curly top virus, potato virus, pseudo curly top virus, tomato bushy stunt virus, tobacco etch virus, cucumber mosaic virus, tomato mosaic virus (ToMV), tomato mottle gemini virus, alfalfa mosaic virus, tomato spotted wilt virus, tomato yellow leaf curl virus, tomato yellow top virus.

116. The method of clause 115, wherein the viral disease is caused by a virus selected from the group consisting of Beet Curly Top Virus and Tomato Yellow Leaf Curl Virus.

117. The method of any one of clauses 66 to 114, wherein the long-term disease tolerance comprises a fungal disease tolerance and a bacterial disease tolerance.

118. The method of any one of clauses 66 to 111 or clauses 115 to 117, wherein the long-term disease tolerance comprises a fungal disease tolerance and a viral disease tolerance.

119. The method of clause any one of clauses 66 to 108 or clauses 112 to 117, wherein the long-term disease tolerance comprises a bacterial disease tolerance and a viral disease tolerance.

120. The method of any one of clauses 66 to 120, wherein the long-term disease tolerance comprises a fungal disease tolerance, a bacterial disease tolerance, and a viral disease tolerance.

121. The method of any one of clauses 66 to 121, wherein the long-term disease tolerance is conferred via contacting the crop plant with the composition prior to transplantation of the crop plant.

122. The method of any one of clauses 66 to 122, wherein the long-term disease tolerance is conferred via contacting the crop plant with the composition in a location selected from the group consisting of a greenhouse, a plant house, and an outdoor plant nursery.

123. The method of any one of clauses 66 to 122, wherein the long-term disease tolerance is conferred via contacting the crop plant with the composition in a greenhouse.

124. The method of any one of clauses 66 to 122, wherein the long-term disease tolerance is conferred via contacting the crop plant with the composition in a plant house.

125. The method of any one of clauses 66 to 122, wherein the long-term disease tolerance is conferred via contacting the crop plant with the composition in an outdoor plant nursery.

126. The method of any one of clauses 66 to 126, wherein the induction of long-term disease tolerance improves crop plant yield.

127. The method of any one of clauses 66 to 127, wherein the induction of long-term disease tolerance reduces pesticide use on the crop plant.

128. The method of any one of clauses 66 to 128, wherein appearance of the long-term disease tolerance is observed between 6-12 weeks after transplant of the crop plant into a field.

129. The method of any one of clauses 66 to 129, wherein appearance of the long-term disease tolerance is observed between 10-12 weeks after transplant of the crop plant into a field.

130. The method of any one of clauses 66 to 130, wherein the long-term disease tolerance is present between 6-12 weeks after contacting the crop plant with the composition.

131. The method of any one of clauses 66 to 131, wherein the long-term disease tolerance is present between 10-12 weeks after contacting the crop plant with the composition.

1. A method of improving disease tolerance of a crop plant, said method comprising the step of: contacting the crop plant with a composition comprising at least one cyclopropene, wherein contacting the crop plant with the composition results in an improvement of long-term disease tolerance of the crop plant.

In one aspect of the present disclosure, a method of improving disease tolerance of a crop plant is provided. The method comprises the step of contacting the crop plant with a composition comprising at least one cyclopropene, wherein contacting the crop plant with the composition results in an improvement of long-term disease tolerance of the crop plant.

As used herein, the term "contacting" refers to any method that allows for the disclosed composition to contact crop plants. Examples of such contact methods may include, for example, spraying, gassing, foaming, fogging, pouring, brushing, dipping, applying granules, similar methods, or combinations thereof. As used herein, the term "crop plant" refers to plants that are grown for the purpose of removing one or more plant parts, when such parts are considered a useful product.

As used herein, the term "cyclopropene" means and includes any compound with the following formula

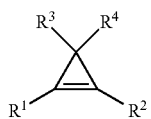

where each $R^1$, $R^2$, $R^3$ and $R^4$ is independently selected from the group consisting of H and a chemical group of the formula -(L)$_n$-Z wherein:

n is an integer from 0 to 12;

each L is independently selected from the group consisting of D1, D2, E, and J;

where D1 is of the formula

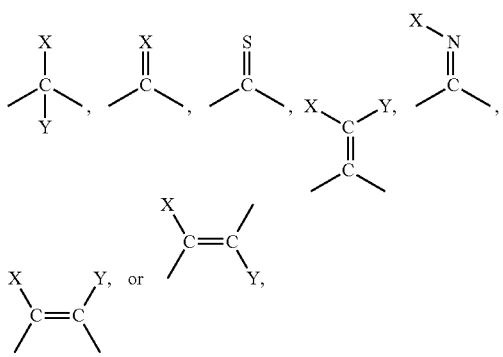

where D2 is of the formula

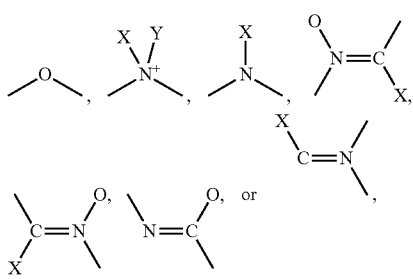

where E is of the formula

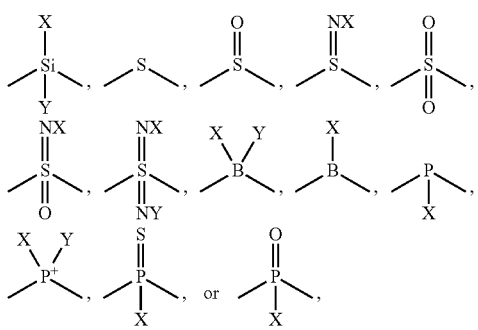

where J is of the formula:

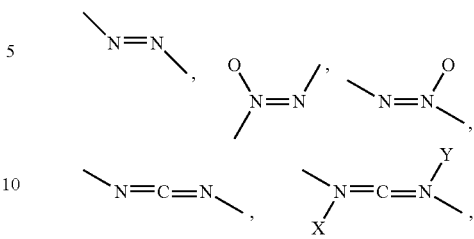

or —C≡C—, where each X and Y is independently a chemical group of the formula

-(L)$_m$-Z, m is an integer from 0 to 8, and no more than two D2 or E groups are adjacent to each other and no J groups are adjacent to each other; and each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system, where the total number of heteroatoms in -(L)$_n$-Z is from 0 to 6, and where the total number of non-hydrogen atoms in the compound is 50 or less.

For the purposes of this disclosure, in the structural representations of the various L groups, each open bond indicates a bond to another L group, a Z group, or the cyclopropene moiety. For example, the structural representation

indicates an oxygen atom with bonds to two other atoms; it does not represent a dimethyl ether moiety.

Among embodiments in which at least one of $R^1$, $R^2$, $R^3$ and $R^4$ is not hydrogen and has more than one L group, the L groups within that particular $R^1$, $R^2$, $R^3$ or $R^4$ group may be the same as the other L groups within that same $R^1$, $R^2$, $R^3$ or $R^4$ group, or any number of L groups within that particular $R^1$, $R^2$, $R^3$ or $R^4$ group may be different from the other L groups within that same $R^1$, $R^2$, $R^3$ or $R^4$ group.

Among embodiments in which at least one of $R^1$, $R^2$, $R^3$ and $R^4$ contains more than one Z group, the Z groups within that $R^1$, $R^2$, $R^3$ or $R^4$ group may be the same as the other Z groups within that $R^1$, $R^2$, $R^3$ or $R^4$ group, or any number of Z groups within that $R^1$, $R^2$, $R^3$ or $R^4$ group may be different from the other Z groups within that $R^1$, $R^2$, $R^3$ or $R^4$ group.

$R^1$, $R^2$, $R^3$ and $R^4$ groups are independently selected from the suitable groups. $R^1$, $R^2$, $R^3$, and $R^4$ groups may be the same as each other, or any number of them may be different from the others. Examples of groups that are suitable for use as one or more of $R^1$, $R^2$, $R^3$ and $R^4$ may include, but are not limited to, aliphatic groups, cycloaliphatic groups, aliphaticoxy groups, alkylphosphonato groups, alkylsulfonyl groups, cycloalkylsulfonyl groups, alkylamino groups, cycloalkylamino groups, alkylaminosulfonyl groups, alkylcarbonyl groups, heterocyclic groups, aryl groups, heteroaryl groups, halogens, silyl groups, other groups, and mixtures and combinations thereof. Groups that are suitable for use as one or more of $R^1$, $R^2$, $R^3$ and $R^4$ may be substituted or unsubstituted. Independently, groups that are suitable for use as one or more of $R^1$, $R^2$, $R^3$ and $R^4$ may be connected directly to the cyclopropene ring or may be connected to the cyclopropene ring through an intervening group such as, for example, a heteroatom-containing group.

Examples of aliphatic groups may include, but are not limited to, alkyl, alkenyl, and alkynyl groups. Suitable aliphatic groups may be substituted or unsubstituted. Some suitable substituted aliphatic groups may include, but are not limited to, acetylaminoalkenyl, acetylaminoalkyl, acetylaminoalkynyl, alkoxyalkoxyalkyl, alkoxy alkenyl, alkoxyalkyl, alkoxyalkynyl, alkoxycarbonylalkenyl, alkoxycarbonylalkyl, alkoxy carbonylalkynyl, alkylcarbonyloxyalkyl, alkyl (alkoxyimino)alkyl, carboxyalkenyl, carboxyalkyl, carboxyalkynyl, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylaminoalkyl, alkylsulfonylalkyl, alkylthioalkenyl, alkylthioalkyl, alkylthioalkynyl, haloalkylthioalkenyl, haloalkylthioalkyl, or haloalkylthioalkynyl.

Examples of aliphatic-oxy groups may include, but are not limited to, alkenoxy, alkoxy, alkynoxy, and alkoxycarbonyloxy. Examples of alkylphosphonato groups may include, but are not limited to, alkylphosphonato, dialkylphosphato, or dialkylthiophosphato. Non-limiting example of alkylamino groups may be dialkylamino or monalkylamino. Non-limiting example of alkylsulfonyl groups may be dialkylamino sulfonyl.

Examples of cycloaliphatic groups may include, but are not limited to, cycloalkenyl, cycloalkyl, and cycloalkynyl. Suitable cycloaliphatic groups may be substituted or unsubstituted. Among the suitable substituted cycloaliphatic groups are, for example, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, haloalkylthiocycloalkenyl, haloalkylthiocycloalkyl, or haloalkylthiocycloalkynyl.

Examples of heterocyclyl groups (i.e., non-aromatic cyclic groups with at least one heteroatom in the ring) may include, but are not limited to, substituted or unsubstituted cycloalkylsulfonyl groups or cycloalkylamino groups, such as, for example, dicycloalkylaminosulfonyl or dicycloalkylamino. Suitable substituted heterocyclyl groups may be substituted or unsubstituted. Among the suitable substituted heterocyclyl groups are, for example, alkenylheterocyclyl, alkylheterocyclyl, alkynylheterocyclyl, acetylaminoheterocyclyl, alkoxyalkoxyheterocyclyl, alkoxyheterocyclyl, alkoxycarbonylheterocyclyl, alkylcarbonyloxyheterocyclyl, carboxyheterocyclyl, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, or haloalkylthioheterocyclyl.

Examples of substituted and unsubstituted heterocyclyl groups that are connected to the cyclopropene compound through an intervening oxy group, amino group, carbonyl group, or sulfonyl group may include, but are not limited to, heterocyclylcarbonyl, diheterocyclylamino, or diheterocyclylamino sulfonyl.

Examples of substituted and unsubstituted aryl groups may include, but are not limited to, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, and haloalkylthioaryl.

Examples of heteroaryl groups may include, but are not limited to, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, or haloalkylthioheteroaryl.

Examples of substituted and unsubstituted heteroaryl groups that are connected to the cyclopropene compound through an intervening oxy group, amino group, carbonyl group, sulfonyl group, thioalkyl group, or aminosulfonyl group may include, but are not limited to, diheteroarylamino, heteroarylthioalkyl, or diheteroarylaminosulfonyl.

Further examples of suitable $R^1$, $R^2$, $R^3$ and $R^4$ groups may include, but are not limited to, hydrogen, fluoro, chloro, bromo, iodo, cyano, nitro, nitroso, azido, chlorato, bromato, iodato, isocyanato, isocyanido, isothiocyanato, pentafluorothio, acetoxy, carboethoxy, cyanato, nitrato, nitrito, perchlorato, allenyl, butylmercapto, diethyl phosphonato, dimethylphenylsilyl, isoquinolyl, mercapto, naphthyl, phenoxy, phenyl, piperidino, pyridyl, quinolyl, triethylsilyl, trimethylsilyl, or substituted analogs thereof.

As used herein, the chemical group G is a 3 to 14 membered ring system. Ring systems suitable as chemical group G may be substituted or unsubstituted. Further, they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, or fused. Among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated three-membered ring, such as, for example, a substituted or unsubstituted cyclopropane, cyclopropene, epoxide, or aziridine ring.

In some embodiments, G is a ring system that contains a four membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from chemical groups in the category X as defined herein below. Also suitable are embodiments in which G is a carbocyclic ring system.

Examples of suitable G groups may include, but are not limited to, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl) phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl, 5-methyl-6-chromanyl, adamantyl, norbornyl, or their substituted analogs such as, for example: 3-butyl-pyridin-2-yl, 4-bromo-pyridin-2-yl, 5-carboethoxy-pyridin-2-yl, or 6-methoxyethoxy-pyridin-2-yl.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

In some embodiments, one or more cyclopropenes are used in which one or more of $R^1$, $R^2$, $R^3$ and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$ and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$ and $R^4$ is a structure that has no halogen atom substituent. Independently, in some embodiments, one or more of $R^1$, $R^2$, $R^3$ and $R^4$ is a structure that has no substituent that is ionic. Independently, in some embodiments, one or more of $R^1$, $R^2$, $R^3$ and $R^4$ is a structure that is not capable of generating oxygen compounds.

In some embodiments of the disclosure, one or more of $R^1$, $R^2$, $R^3$ and $R^4$ is hydrogen or $(C_1-C_{10})$ alkyl. In some embodiments, each of $R^1$, $R^2$, $R^3$ and $R^4$ is hydrogen or $(C_1-C_8)$ alkyl. In some embodiments, each of $R^1$, $R^2$, $R^3$ and $R^4$ is hydrogen or $(C_1-C_4)$ alkyl. In some embodiments, each of $R^1$, $R^2$, $R^3$ and $R^4$ is hydrogen or methyl. When $R^1$ is methyl and each of $R^2$, $R^3$, and $R^4$ is hydrogen, the cyclopropene is known herein as 1-methylcyclopropene (1-MCP). In some embodiments of the present disclosure, the cyclopropene is 1-methylcyclopropene (1-MCP).

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this disclosure may be prepared by any method. Some suitable methods of preparation of cyclopropenes are the processes disclosed in U.S. Pat. Nos. 5,518,988 and 6,017,849. Any compound that is not a cyclopropene is known herein as a "non-cyclopropene."

In various embodiments, the crop is a monocot crop. As used herein, a "monocot" crop refers to a plant with seeds that contain one embryonic leaf (cotyledon). In other embodiments, the crop is a dicot crop. As used herein, a "dicot" crop refers to a plant with seeds that contain two embryonic leaves (cotyledons). In some embodiments, the crop is corn. In other embodiments, the crop is soybean.

In various embodiments, the crop is a vegetable. In certain aspects, the crop is a solanaceous crop. In some embodiments, the solanaceous crop is selected from the group consisting of tomato, pepper, eggplant, white potato, red potato, and tomatillo. In one embodiment, the solanaceous crop is tomato. In another embodiment, the solanaceous crop is pepper. In yet another embodiment, the solanaceous crop is eggplant. In some embodiments, the solanaceous crop is white potato. In another embodiment, the solanaceous crop is red potato. In yet another embodiment, the solanaceous crop is tomatillo.

In other aspects, the crop is a member of the Cucurbitacea family. In some embodiments, the member of the Cucurbitacea family is cucumber. In other embodiments, the member of the Cucurbitacea family is melon. In yet other embodiments, the member of the Cucurbitacea family is watermelon.

In certain aspects, the crop is a cruciferae crop, also known as cruciferous vegetables of the family Brassicaceae. In various embodiments, the cruciferae crop is cabbage. In other embodiments, the cruciferae crop is broccoli. In yet other embodiments, the cruciferae crop is cauliflower.

In various aspects, the plant is a seedling. As used herein, the term "seedling" refers to a young plant sporophyte developing out of a plant embryo from a seed. Seedling development starts with germination of the seed, which is commonly performed in a controlled environment, e.g., greenhouse, hotbed, cold frame.

In some embodiments, the plant is a pre-transplant plant. The term "pre-transplant" refers to a point in time prior to transplantation of a plant. As used herein, the term "transplanting" or grammatical variations thereof refers to moving a plant from one location and replanting it at another location. In some embodiments, the long-term disease tolerance is conferred via contacting the crop plant with the composition prior to transplantation of the crop plant. In certain aspects, the plant is a greenhouse plant.

In some embodiments, the composition is a liquid composition. Such compositions may be liquid at a temperature of 25° C. In some embodiments, the composition is liquid at the temperature at which the composition is used to treat plants. Because plants are often treated outside of any buildings, plants may be treated at temperatures ranging from about 1° C. to about 45° C. Suitable liquid compositions need not be liquid over such entire range, but they are liquid at some temperature from about 1° C. to about 45° C.

The liquid composition of present disclosure may be a single pure substance, or it may contain more than one substance. If containing more than one substance, the liquid composition may be a solution or a dispersion or a combination thereof. If, in the liquid composition, one substance is dispersed in another substance in the form of a dispersion, the dispersion may be of any type, including, for example, a suspension, a latex, an emulsion, a miniemulsion, a microemulsion, or any combination thereof.

The amount of cyclopropene in the liquid composition may vary widely, depending on the type of composition and the intended method of use. In some embodiments, the amount of cyclopropene, based on the total weight of the composition, is 4% by weight or less; or 1% by weight or less; or 0.5% by weight or less; or 0.05% by weight or less. Independently, in some embodiments, the amount of cyclopropene, based on the total weight of the composition, is 0.000001% by weight or more; or 0.00001% by weight or more; or 0.0001% by weight or more; or 0.001% by weight or more.

Among embodiments of the present disclosure that use a liquid composition comprising water, the amount of cyclopropene may be characterized as parts per million (i.e., parts by weight of cyclopropene per 1,000,000 parts by weight of water in the composition, "ppm") or as parts per billion (i.e., parts by weight of cyclopropene per 1,000,000,000 parts by weight of water in the composition, "ppb"). In some embodiments, the amount of cyclopropene is 1 ppb or more; or 10 ppb or more; or 100 ppb or more. Independently, in some embodiments, the amount of cyclopropene is 10,000 ppm or less; or 1,000 ppm or less.

In some embodiments, the composition may further include at least one molecular encapsulating agent. Independently, in some embodiments, the composition may not include any molecular encapsulating agent. When a molecular encapsulating agent is used, suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the disclosure, the encapsulating agent is alpha-cyclodextrin, beta-cyclodextrin, gamma-cyclodextrin, or a mixture thereof. In some embodiments, particularly when the cyclopropene is 1-methylcyclopropene, the encapsulating agent is alpha-cyclodextrin. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof may also be utilized pursuant to the present disclosure. Some cyclodextrins are available, for example, from Wacker Biochem Inc., Adrian, Mich. or Cerestar USA, Hammond, Ind., as well as other vendors.

In some of the embodiments in which a molecular encapsulating agent is present, at least one molecular encapsulating agent encapsulates one or more cyclopropene. A cyclopropene or substituted cyclopropene molecule encapsulated in a molecule of a molecular encapsulating agent is known herein as a "cyclopropene molecular encapsulating agent complex." In some embodiments, the composition of present disclosure is a liquid composition in which some or all of the cyclopropene is encapsulated in one or more encapsulating agent. The cyclopropene molecular encapsulation agent complexes may be prepared by any means.

In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

In some embodiments, the composition comprises at least one cyclopropene and at least one molecular encapsulating agent. In some of such embodiments, the amount of molecular encapsulating agent may usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

In some embodiments, the liquid composition further comprises a solvent. In various embodiments, the solvent is water.

In certain aspects, the composition is a granular composition. In some embodiments, the granular composition is a powder.

In certain aspects, the composition is a gaseous composition. In such embodiments, crop plants may be surrounded by a normal ambient atmosphere (at approximately one atmosphere pressure) to which the composition of present disclosure has been added. In some embodiments, the concentration of cyclopropene is 0.1 nl/l (i.e., nanoliter per liter) or higher; or 1 nl/l or higher, or 10 nl/l or higher; or 100 nl/l or higher. Independently, in some embodiments, the concentration of cyclopropene is 3,000 nl/l or lower; or 1,000 nl/l or lower.

In various embodiments, the contacting is performed by a method selected from the group consisting of spraying, gassing, foaming, fogging, pouring, brushing, dipping, applying granules, similar methods, and combinations thereof. In some embodiments, the contacting is performed via spraying. In other embodiments, the contacting is performed via spreading.

In some aspects, the long-term disease tolerance is a reduction in disease incidence of the crop plant. For instance, a crop plant with reduced disease incidence produced by the methods of present disclosure may have a level of reduced incidence of a disease compared to crop plants produced without the methods of present disclosure, as judged by the quality criteria appropriate for that crop plant.

In some aspects, the long-term disease tolerance is a reduction in disease severity of the crop plant. For instance, a crop plant with reduced disease severity produced by the methods of present disclosure may have a level of reduced severity of a disease compared to crop plants produced without the methods of present disclosure, as judged by the quality criteria appropriate for that crop plant.

In various aspects, the long-term disease tolerance is a fungal disease tolerance. In some embodiments, the fungal disease is caused by a fungus selected from the group consisting of *Alternaria alternata* f sp. *lycopersici, Colletotrichum coccodes, Colletotrichum dematium, Colletotrichum gloeosporioides, Glomerella cingulate, Alternaria alternate, Stemphylium botryosum, Pleospora tarda, Stemphylium herbarum, Pleospora herbarum, Pleospora lycopersici, Ulocladium consortiale, Stemphylium consortiale, Thielaviopsis basicola, Chalara elegans, Alternaria alternate, Phytophthora capsici, Phytophthora drechsleri, Phytophthora nicotianae* var. *parasitica, Phytophthora para-* sitica, Pseudocercospora fuligena, Cercospora fuligena, Macrophomina phaseolina, Pyrenochaeta lycopersici, Didymella lycopersici, Alternaria solani, Fusarium oxysporum f. sp. radicis-lycopersici, Fusarium oxysporum f. sp. lycopersici, Stemphylium botryosum f. sp. lycopersici, Stemphylium lycopersici, Stemphylium floridanum, Stemphylium solani, Botrytis cinerea, Botryotinia fuckeliana, Phytophthora infestans, Fulvia fulva, Cladosporium flavum, Phoma destructiva, Oidiopsis sicula, Leveillula taurica, Pythium aphanidermatum, Pythium arrhenomanes, Pythium debaryanum, Pythium myriotylum, Pythium ultimum, Rhizoctonia solani, Thanatephorus cucumeris, Rhizopus stolonifer, Septoria lycopersici, Geotrichum candidum, Galactomyces geotrichum, Geotrichum klebahnii, Geotrichum penicillatum, Sclerotium rolfsii, Athelia rolfsii, Corynespora cassiicola, Verticillium albo-atrum, Verticillium dahliae, Sclerotinia sclerotiorum, and Sclerotinia minor. In other embodiments, the fungal disease is caused by a fungus selected from the group consisting of Alternaria tomatophila, Pythium sp., and Pseudoperonospora cubensis.

Fungal diseases that may be targeted according to the methods of the present disclosure include those listed in Table 1.

TABLE 1

Fungal diseases and causative pathogens

| | |
|---|---|
| Alternaria stem canker | Alternaria alternata f. sp. lycopersici |
| Anthracnose | Colletotrichum coccodes |
| | Colletotrichum dematium |
| | Colletotrichum gloeosporioides |
| | Glomerella cingulata [teleomorph] |
| Black mold rot | Alternaria alternata |
| | Stemphylium botryosum |
| | Pleospora tarda [teleomorph] |
| | Stemphylium herbarum |
| | Pleospora herbarum [teleomorph] |
| | Pleospora lycopersici |
| | Ulocladium consortiale |
| | Stemphylium consortiale |
| Black root rot | Thielaviopsis basicola |
| | Chalara elegans [synanamorph] |
| Black shoulder | Alternaria alternata |
| Buckeye fruit and root rot | Phytophthora capsici |
| | Phytophthora drechsleri |
| | Phytophthora nicotianae var. parasitica |
| | Phytophthora parasitica |
| Cercospora leaf mold | Pseudocercospora fuligena |
| | Cercospora fuligena |
| Charcoal rot | Macrophomina phaseolina |
| Corky root rot | Pyrenochaeta lycopersici |
| Didymella stem rot | Didymella lycopersici |
| Early blight | Alternaria solani |
| Fusarium crown and root rot | Fusarium oxysporum f.sp. radicis-lycopersici |
| Fusarium wilt | Fusarium oxysporum f.sp. lycopersici |
| Gray leaf spot | Stemphylium botryosum f.sp. lycopersici |
| | Stemphylium lycopersici |
| | Stemphylium floridanum |
| | Stemphylium solani |
| Gray mold | Botrytis cinerea |
| | Botryotinia fuckeliana [teleomorph] |
| Late blight | Phytophthora infestans |
| Leaf mold | Fulvia fulva |
| | Cladosporium fulvum |
| Phoma rot | Phoma destructiva |
| Powdery mildew | Oidiopsis sicula |
| | Leveillula taurica [teleomorph] |
| Pythium damping-off and fruit rot | Pythium aphanidermatum |
| | Pythium arrhenomanes |
| | Pythium debaryanum |
| | Pythium myriotylum |
| | Pythium ultimum |
| Rhizoctonia damping-off and fruit rot | Rhizoctonia solani |
| | Thanatephorus cucumeris [teleomorph] |

TABLE 1-continued

Fungal diseases and causative pathogens

| | |
|---|---|
| Rhizopus rot | Rhizopus stolonifer |
| Septoria leaf spot | Septoria lycopersici |
| Sour rot | Geotrichum candidum |
| | Galactomyces geotrichum [teleomorph] |
| | Geotrichum klebahnii (= G. penicillatum) |
| Southern blight | Sclerotium rolfsii |
| | Athelia rolfsii [teleomorph] |
| Target spot | Corynespora cassiicola |
| Verticillium wilt | Verticillium albo-atrum |
| | Verticillium dahliae |
| White mold | Sclerotinia sclerotiorum |
| | Sclerotinia minor |

In certain aspects, the long-term disease tolerance is a bacterial disease tolerance. In some embodiments, the bacterial disease is caused by a bacteria selected from the group consisting of Clavibacter michiganensis subsp. michiganensis, Pseudomonas syringae pv. tomato, Xanthomonas campestris pv. vesicatoria, Erwinia carotovora subsp. carotovora, Ralstonia solanacearum, Pseudomonas corrugata, and Pseudomonas syringae pv. syringae. In other embodiments, the bacterial disease is caused by a bacteria selected from the group consisting of Corynespora cassiicola, Xanthomonas euvesicatoria, Xanthomonas perforans, [Xanthomonas axonopodis (syn. campestris) pv. vesicatoria], Xanthomonas vesicatoria, and Xanthomonas gardneri.

Bacterial diseases that may be targeted according to the methods of the present disclosure include those listed in Table 2.

TABLE 2

Bacterial diseases and causative pathogens

| | |
|---|---|
| Bacterial canker | Clavibacter michiganensis subsp. michiganensis |
| Bacterial speck | Pseudomonas syringae pv. tomato |
| Bacterial spot | Xanthomonas campestris pv. vesicatoria |
| Bacterial stem rot and fruit rot | Xanthomonas campestris pv. vesicatoria |
| Bacterial wilt | Erwinia carotovora subsp. carotovora |
| Pith necrosis | Ralstonia solanacearum |
| Syringae leaf spot | Pseudomonas corrugata |

In other aspects, the long-term disease tolerance is a viral disease tolerance. In some embodiments, the viral disease is caused by a virus selected from the group consisting of tobacco mosaic virus (TMV), curly top virus, potato virus, pseudo curly top virus, tomato bushy stunt virus, tobacco etch virus, cucumber mosaic virus, tomato mosaic virus (ToMV), tomato mottle gemini virus, alfalfa mosaic virus, tomato spotted wilt virus, tomato yellow leaf curl virus, tomato yellow top virus. In other embodiments, the viral disease is caused by a virus selected from the group consisting of Beet Curly Top Virus and Tomato Yellow Leaf Curl Virus.

Viral diseases that may be targeted according to the methods of the present disclosure include those listed in Table 3.

TABLE 3

Viral diseases and causative pathogens

| | |
|---|---|
| Common mosaic of tomato (internal browning of fruit) | Tobacco mosaic virus (TMV) |
| Curly top | Curly top virus |
| Potato virus Y | Potato virus Y |
| Pseudo curly top | Pseudo curly top virus |
| Tomato bushy stunt | Tomato bushy stunt virus |
| Tomato etch | Tobacco etch virus |
| Tomato fern leaf | Cucumber mosaic virus |
| Tomato mosaic | Tomato mosaic virus (ToMV) |
| Tomato mottle | Tomato mottle gemini virus |
| Tomato necrosis | Alfalfa mosaic virus |
| Tomato spotted wilt | Tomato spotted wilt virus |
| Tomato yellow leaf curl | Tomato yellow leaf curl virus |
| Tomato yellow top | Tomato yellow top virus |

In some aspects, the long-term disease tolerance comprises a fungal disease tolerance and a bacterial disease tolerance. In other aspects, the long-term disease tolerance comprises a fungal disease tolerance and a viral disease tolerance. In yet other aspects, the long-term disease tolerance comprises a bacterial disease tolerance and a viral disease tolerance. In certain aspects, the long-term disease tolerance comprises a fungal disease tolerance, a bacterial disease tolerance, and a viral disease tolerance.

In certain embodiments, the long-term disease tolerance is conferred via contacting the crop plant with the composition in a location selected from the group consisting of a greenhouse, a plant house, and an outdoor plant nursery. In some embodiments, the long-term disease tolerance is conferred via contacting the crop plant with the composition in a greenhouse. In other embodiments, the long-term disease tolerance is conferred via contacting the crop plant with the composition in a plant house. In yet other embodiments, the long-term disease tolerance is conferred via contacting the crop plant with the composition in an outdoor plant nursery.

The disclosed method improves the long-term disease tolerance of the crop plant. In some aspects, the improvement of long-term disease tolerance improves crop plant yield. As used herein, the term "crop plant yield" refers to the amount (herein called "crop amount") of useful plant parts collected from a defined group of crop plants. In one useful definition of the crop yield, the defined group of plants is the group that occupies a certain area of ground (this definition is often used when plants are growing in a contiguous group in a field). In another useful definition of the crop yield, the defined group of plants is a specific number of individually identified plants (this definition may be used for any group of plants, including, for example, plants in fields, in pots, in greenhouses, or any combination thereof).

The crop amount may be defined in a variety of ways. In the practice of the present disclosure, the crop amount may be measured, for example, by any of the following methods: weight, volume, number of harvested plant parts, or biomass. Also contemplated are methods in which the crop amount is measured as the amount in the crop of a specific constituent (such as, for example, sugar, starch, or protein). Further contemplated are methods in which the crop amount is measured as the amount of a certain characteristic (such as, for example, redness, which is sometimes used to measure the amount of a crop of tomatoes). Additionally contemplated are methods in which the crop amount is measured as the amount of a specific portion of the harvested plant part (such as, for example, the number of kernels or the weight of kernels, which are sometimes used to measure the amount of a crop of corn; or the weight of lint, which is sometimes used to measure the amount of a cotton crop).

In some embodiments, the crop yield is defined as the crop amount per unit of area of land. That is, the land area from which the crop was harvested is measured, and the crop amount is divided by the land area to calculate the crop yield. For example, a crop amount measured as the weight of harvested plant parts would lead to a crop yield that is reported as a weight per area (for example, kilograms per hectare).

A few illustrative (but not limiting) examples of crop amount are, for example, total weight of crop harvested; total number of plant parts harvested; weight (or number) of harvested plant parts that each meet or exceed some minimum weight for that type of plant part; or weight (or number) of harvested plant parts that each meet or exceed some minimum quality criterion (e.g., color or flavor or texture or other criterion or combination of criteria) for that type of plant part; weight (or number) of harvested plant parts that are edible; or weight (or number) of harvested plant parts that are able to be sold. In each case, as defined herein above, the crop yield is the crop amount per unit area of land on which the crop was grown.

The methods of present disclosure may increase the crop yield of that group of plants, compared to the crop yield that would have been obtained from that group of plants if it had not been treated with the methods of present disclosure. The increase in crop yield may be obtained in any of a wide variety of ways. For example, one way an increase in crop yield may be obtained is that each plant may produce a greater number of useful plant parts. As another example, one way an increase in crop yield may be obtained is that each useful plant part may have higher weight (e.g., is larger). As a third example, crop yield may increase when a larger number of potentially useful plant parts meets the minimum criteria for acceptable quality. Other ways of increasing the crop yield may also result from the practice of the present disclosure.

In other aspects, the improvement of long-term disease tolerance reduces pesticide use on the crop plant. For instance, a reduction of pesticide use on a crop plant according to the methods of present disclosure may have a level of reduced volume or frequency of pesticide application compared to crop plants produced without the methods of present disclosure, as judged by the usage criteria appropriate for that crop plant.

In certain embodiments, the long-term disease tolerance is present between 6-12 weeks after contacting the crop plant with the composition. In other embodiments, the long-term disease tolerance is present between 10-12 weeks after contacting the crop plant with the composition. In one embodiment, the long-term disease tolerance is present at about 6 weeks after contacting the crop plant with the composition. In another embodiment, the long-term disease tolerance is present at about 7 weeks after contacting the crop plant with the composition. In yet another embodiment, the long-term disease tolerance is present at about 8 weeks after contacting the crop plant with the composition. In one embodiment, the long-term disease tolerance is present at about 9 weeks after contacting the crop plant with the composition. In another embodiment, the long-term disease tolerance is present at about 10 weeks after contacting the crop plant with the composition. In yet another embodiment, the long-term disease tolerance is present at about 11 weeks after contacting the crop plant with the composition. In another embodiment, the long-term disease tolerance is present at about 12 weeks after contacting the crop plant with the composition.

In certain embodiments, the long-term disease tolerance is observed between 6-12 weeks after contacting the crop plant with the composition. In other embodiments, the long-term disease tolerance is observed between 10-12 weeks after contacting the crop plant with the composition. In one embodiment, the long-term disease tolerance is observed at about 6 weeks after contacting the crop plant with the composition. In another embodiment, the long-term disease tolerance is observed at about 7 weeks after contacting the crop plant with the composition. In yet another embodiment, the long-term disease tolerance is observed at about 8 weeks after contacting the crop plant with the composition. In one embodiment, the long-term disease tolerance is observed at about 9 weeks after contacting the crop plant with the composition. In another embodiment, the long-term disease tolerance is observed at about 10 weeks after contacting the crop plant with the composition. In yet another embodiment, the long-term disease tolerance is observed at about 11 weeks after contacting the crop plant with the composition. In another embodiment, the long-term disease tolerance is observed at about 12 weeks after contacting the crop plant with the composition In another aspect of the present disclosure, a method of inducing disease tolerance of a crop plant is provided. The method comprises the step of contacting the crop plant with a composition comprising at least one cyclopropene, wherein contacting the crop plant with the composition results in an induction of long-term disease tolerance of the crop plant. The embodiments describing the method of improving disease tolerance of a crop plant provided herein are also applicable to the method of inducing disease tolerance of a crop plant.

The disclosed method induces long-term disease tolerance of the crop plant. In some aspects, the induction of long-term disease tolerance improves crop plant yield. In other aspects, the induction of long-term disease tolerance reduces pesticide use on the crop plant.

EXAMPLES

Example 1

Evaluation of Beet Curly Top Virus on Tomatoes

In the instant example, symptoms of infection with Beet Curly Top Virus (BCTV) on tomatoes were evaluated. Plants were either treated with a composition comprising 1-MCP or left untreated.

Tomato seedlings (var Heinz 8504) with 4 leaves (approximately 4 inches tall) in seedling trays were either i) sprayed with a treatment of 1-MCP (4 gm ai/ha) or ii) left untreated. Contacting the plants was achieved using a pressurized backpack spraying system containing 1-MCP and water. Two days later, the tomato seedlings were transplanted into the open field near Five Points, Calif. following normal commercial tomato production practices.

Throughout the growing season, normal field production practices were performed, including fertilization, watering, and pest control (e.g., insecticide, fungicide, and herbicide) applications uniformly to the entire trial area. Approximately eight (8) weeks later, when the tomatoes had grown to approximately 2 feet tall, an infestation of Beet Curly Top Virus (BCTV) was noted. Observations were taken on percentage of plants infected with BCTV in treated and untreated plots.

As shown in Table 4, treatment with 1-MCP significantly reduced the number of plants showing symptoms of infection by BCTV compared to untreated controls.

TABLE 4

| Plant Group | Percentage of BCTV Infested Plants | P = 0.065 |
|---|---|---|
| Treated with 1-MCP | 4% | A |
| Untreated Controls | 9% | B |

Example 2

Evaluation of Tomato Yellow Leaf Curl Virus (Begomovirus Geminiviridae) on Tomatoes In the instant example, symptoms of infection with Tomato Yellow Leaf Curl Virus (TYLCV) on tomatoes were evaluated. Plants were either treated with a composition comprising 1-MCP or left untreated.

Tomato seedlings (var Florida 47) with approximately 4 leaves (approximately 4 inches tall) in seedling trays were either i) sprayed with 1-MCP (50 ppm ai) or ii) left untreated. Contacting the plants was achieved using a watering can containing 1-MCP and water. Three days later, the seedlings were transplanted into the open field near Myakka City, Fla. following normal commercial tomato production practices.

Throughout the growing season, normal field production practices were performed, including fertilization, watering, and pest control (e.g., insecticide, fungicide, and herbicide) applications uniformly to the entire trial area. Approximately 9 weeks later, when the tomatoes had grown to approximately 3 feet tall, an infestation of Tomato Yellow Leaf Curl Virus was observed. In each plot of plants that were treated with 1-MCP, and the corresponding plot of plants that were untreated, counts were made of the number of plants showing symptoms of infection by TYLCV out of the total of 54 plants per plot.

As shown in Table 5, treatment with 1-MCP significantly reduced the number of plants showing symptoms of infection by TYLCV.

TABLE 5

| Plant Group | P = 0.081 | Mean |
|---|---|---|
| Untreated Controls | A | 20% |
| Treated with 1-MCP | B | 11% |

Example 3

Evaluation of Target Spot Bacterial Infection (*Corynespora cassiicola*) on Tomatoes In the instant example, symptoms of Target Spot bacterial infection (*Corynespora cassiicola*) on tomatoes were evaluated. Plants were either treated with a composition comprising 1-MCP or left untreated.

Tomato seedlings (var HM 1823) with approximately 4 leaves (approximately 4 inches tall) in seedling trays were either i) sprayed with 1-MCP (50 ppm ai) or ii) left untreated. Contacting the plants was achieved using a watering can containing 1-MCP and water. Three days later, the seedlings were transplanted into the open field near Myakka City, Fla. following normal commercial tomato production practices.

Throughout the growing season, normal field production practices were performed, including fertilization, watering, and pest control (e.g., insecticide, fungicide, and herbicide) applications uniformly to the entire trial area. Approximately 9 weeks later, when the tomatoes had grown to approximately 3 feet tall, an infestation of Target Spot was observed. In each plot of plants that were treated with 1-MCP, and the corresponding plot of plants that were untreated, counts were made of the number of plants showing symptoms of infection by Target Spot out of the total of 54 plants per plot.

As shown in Table 6, treatment with 1-MCP significantly reduced the number of plants showing symptoms of infection by Target Spot.

TABLE 6

| Plant Group | P = 0.003 | Percentage of Infected Plants |
|---|---|---|
| Untreated Controls | A | 41% |
| Treated with 1-MCP | B | 19% |

Example 4

Evaluation of Bacterial Spot (*Xanthomonas euvesicatoria* and *Xanthomonas perforans*=[*Xanthomonas axonopodis* (Syn. Campestris) Pv. *Vesicatoria*], *Xanthomonas vesicatoria*, and *Xanthomonas gardneri*) on Tomatoes In the instant example, symptoms of Bacterial Spot bacterial infection (*Xanthomonas euvesicatoria* and *Xanthomonas perforans*=[*Xanthomonas axonopodis* (syn. *campestris*) pv. *vesicatoria*], *Xanthomonas vesicatoria*, and *Xanthomonas gardneri*) on tomatoes were evaluated. Plants were either treated with a composition comprising 1-MCP or left untreated.

Tomato Seedlings (var Charger) with approximately 4 leaves (approximately 4-5 inches tall) in seedling trays were either i) sprayed with 1-MCP (1-40 g ai/ha) or ii) left untreated. Contacting the plants was achieved using pressurized backpack sprayer. Two days later, the seedlings were transplanted into the open field near Thonotosassa, Fla. following normal commercial tomato production practices.

Throughout the growing season, normal field production practices were performed, including fertilization, watering, and pest control (e.g., insecticide, fungicide, and herbicide) applications uniformly to the entire trial area. Approximately 3 weeks later, when the tomatoes had grown to approximately 1½ feet tall an infestation of Bacterial Spot was observed. In each plot of plants that were treated with 1-MCP, and the corresponding plot of plants that were untreated, disease severity assessments were made.

As shown in Table 7, treatment with 1-MCP significantly reduced the number of plants showing symptoms of infection by the Bacterial Spot.

TABLE 7

| Plant Group | p = 0.04 |
|---|---|
| Untreated Controls | 14% |
| Treated with 1-MCP | 4% |

Example 5

Evaluation of Early Blight (*Alternaria tomatophila*) on Tomatoes

In the instant example, symptoms of fungal infection with Early Blight (*Alternaria tomatophila*) on tomatoes were evaluated. Plants were either treated with a composition comprising 1-MCP or left untreated.

Tomato seedlings (var Charger) with approximately 4 leaves (approximately 4-5 inches tall) in seedling trays were either i) sprayed with 1-MCP (1-10 g ai/ha) or ii) left untreated. Contacting the plants was achieved using pressurized backpack sprayer. Two days later, the seedlings were transplanted into the open field near Thonotosassa, Fla. following normal commercial tomato production practices.

Throughout the growing season, normal field production practices were performed, including fertilization, watering, and pest control (e.g., insecticide, fungicide, and herbicide) applications uniformly to the entire trial area. Beginning approximately 3 weeks later, and continuing approximately 7 weeks later and approximately 11 weeks later, the percent disease severity ratings were made in each plot of plants that were treated with 1-MCP and the corresponding plot of plants that were untreated.

As shown in Table 8, treatment with 1-MCP significantly reduced the average percent disease severity ratings for Early Blight across the three dates by approximately 30%.

TABLE 8

| Plant Group | p = 0.09 |
|---|---|
| Untreated Controls | 39.5 |
| Treated with 1-MCP | 27.6 |

Example 6

Evaluation of Root Rot (*Pythium* sp.) on Peppers

In the instant example, symptoms of fungal infection with Root Rot (*Pythium* sp.) on peppers were evaluated. Plants were either treated with a composition comprising 1-MCP or left untreated.

Pepper seedlings with approximately 3 leaves (approximately 4-5 inches tall) in seedling trays were either i) sprayed with 1-MCP (1-10 g ai/ha) or ii) left untreated. Contacting the plants was achieved using a watering can containing a 50 ppm solution of 1-MCP. Three days later, the seedlings were transplanted into the open field near Clinton, N.C. following normal commercial pepper production practices.

Throughout the growing season, normal field production practices were performed, including fertilization, watering, and pest control (e.g., insecticide, fungicide, and herbicide) applications uniformly to the entire trial area.

Treatment of plants with 1-MCP clearly reduced the mortality and stunting of plants that are caused by *Pythium*. Two weeks after transplantation, plants treated with 1-MCP were observed to be slightly larger, darker green, and not as affected by *Pythium* pressure compared to untreated controls. Furthermore, approximately 60 days after transplantation, the differences between the two groups were depicted as shown in FIG. 1.

Example 7

Evaluation of Downy Mildew (*Pseudoperonospora cubensis*) on Cucumbers

In the instant example, symptoms of fungal infection with Downy Mildew (*Pseudoperonospora cubensis*) on cucumbers were evaluated. Plants were either treated with a composition comprising 1-MCP or left untreated.

Cucumber seedlings with approximately 3 leaves (approximately 3 inches tall) in seedling trays were either i) sprayed with 1-MCP (40 g ai/ha) or ii) left untreated. Contacting the plants was achieved using pressurized backpack sprayer. Two days later, the seedlings were transplanted into the open field near Futian Village, Wangsi Township, Dayi County, Sichuan, China, following normal commercial production practices.

Throughout the growing season, normal field production practices were performed, including fertilization, watering, and pest control (e.g., insecticide, fungicide, and herbicide) applications uniformly to the entire trial area. Approximately 5-6 weeks later, the percent disease severity ratings were made in each plot of plants that were treated with 1-MCP and the corresponding plot of plants that were untreated.

As shown in Table 9, treatment with 1-MCP significantly reduced percent disease (Downy Mildew) severity ratings by approximately 47%.

TABLE 9

| Plant Group | p = 0.08 |
| --- | --- |
| Untreated Controls | 34 |
| Treated with 1-MCP | 18 |

What is claimed is:

1. A method of improving long-term disease tolerance of a crop plant, said method comprising:
    contacting the crop plant with a composition comprising 1-methylcyclopropene (1-MCP),
        wherein the crop plant is a pre-transplant seedling having about 3 leaves or about 4 leaves,
        wherein the pre-transplant seedling is a young plant sporophyte that has developed out of a plant embryo from a seed,
    transplanting the pre-transplant seedling, and
    improving the long-term disease tolerance of the crop plant treated with the composition comprising 1-MCP as compared to a crop plant that is not treated with the composition comprising 1-MCP,
        wherein the improvement in the long-term disease tolerance of the treated crop plant is selected from the group consisting of an improvement in a fungal disease tolerance, a bacterial disease tolerance, a viral disease tolerance, or a combination thereof, and
        wherein the long-term disease tolerance is present in the treated crop plant between 6-12 weeks after contacting the pre-transplant seedling with the composition comprising 1-MCP.

2. The method of claim 1, wherein the long-term disease tolerance is a fungal disease tolerance.

3. The method of claim 1, wherein the long-term disease tolerance is a bacterial disease tolerance.

4. The method of claim 1, wherein the long-term disease tolerance is a viral disease tolerance.

5. The method of claim 1, wherein the long-term disease tolerance comprises a fungal disease tolerance, a bacterial disease tolerance, and a viral disease tolerance.

6. The method of claim 1, wherein the long-term disease tolerance is present in the treated crop plant between 10-12 weeks after contacting the pre-transplant seedling with the composition comprising 1-MCP.

7. The method of claim 1, wherein the fungal disease tolerance or the viral disease tolerance are present at about 7 weeks, about 8 weeks, or about 11 weeks after contacting the pre-transplant seedling with the composition comprising 1-MCP.

8. The method of claim 1, wherein the bacterial disease tolerance or the viral disease tolerance are present at about 8 weeks or about 9 weeks after contacting the pre-transplant seedling with the composition comprising 1-MCP.

9. The method of claim 1, wherein the crop plant is a solanaceous crop or a member of the Cucurbitacea family.

10. The method of claim 1, wherein transplanting the pre-transplant seedling occurs about 2 days or about 3 days after contacting the pre-transplant seedling with the composition comprising 1-MCP.

11. A method of inducing long-term disease tolerance of a crop plant, said method comprising:
    contacting the crop plant with a composition comprising 1-methylcyclopropene (1-MCP),
        wherein the crop plant is a pre-transplant seedling having about 3 leaves or about 4 leaves,
        wherein the pre-transplant seedling is a young plant sporophyte that has developed out of a plant embryo from a seed,
    transplanting the pre-transplant seedling, and
    inducing the long-term disease tolerance of the crop plant treated with the composition comprising 1-MCP as compared to a crop plant that is not treated with the composition comprising 1-MCP,
        wherein the improvement of the long-term disease tolerance of the treated crop plant is selected from the group consisting of an improvement in a fungal disease tolerance, a bacterial disease tolerance, a viral disease tolerance, or a combination thereof, and
        wherein the long-term disease tolerance is present in the treated crop plant between 6-12 weeks after contacting the pre-transplant seedling with the composition comprising 1-MCP.

12. The method of claim 11, wherein the long-term disease tolerance is a fungal disease tolerance.

13. The method of claim 11, wherein the long-term disease tolerance is a bacterial disease tolerance.

14. The method of claim 11, wherein the long-term disease tolerance is a viral disease tolerance.

15. The method of claim 11, wherein the long-term disease tolerance comprises a fungal disease tolerance, a bacterial disease tolerance, and a viral disease tolerance.

16. The method of claim 11, wherein the long-term disease tolerance is present in the crop plant between 10-12 weeks after contacting the pre-transplant seedling with the composition comprising 1-MCP.

17. The method of claim 11, wherein the bacterial disease tolerance or the viral disease tolerance are present at about 8 weeks or about 9 weeks after contacting the pre-transplant seedling with the composition comprising 1-MCP.

18. The method of claim 11, wherein the fungal disease tolerance is present at about 7 weeks, about 8 weeks, or about 11 weeks after contacting the pre-transplant seedling with the composition comprising 1-MCP.

19. The method of claim 11, wherein the crop plant is a solanaceous crop or a member of the Cucurbitacea family.

20. The method of claim 11, wherein transplanting the pre-transplant seedling occurs about 2 days or about 3 days after contacting the pre-transplant seedling with the composition comprising 1-MCP.

* * * * *